United States Patent [19]

Derrieu

[11] Patent Number: 5,338,533
[45] Date of Patent: Aug. 16, 1994

[54] CONTROLLED RELEASE DEVICE, AND METHOD OF PREPARATION

[75] Inventor: Guy Derrieu, Cagnes sur Mer, France

[73] Assignee: Laboratoires Virbac, Carros, France

[21] Appl. No.: 888,317

[22] Filed: May 27, 1992

Related U.S. Application Data

[63] Continuation of Ser. No. 634,848, Dec. 27, 1990, abandoned.

[30] Foreign Application Priority Data

Jan. 2, 1990 [FR] France .................. 90 00009

[51] Int. Cl.⁵ ............................................. A01N 25/10
[52] U.S. Cl. ................... 424/411; 424/405; 424/406; 424/409
[58] Field of Search ................ 424/405, 406, 409, 411

[56] References Cited

U.S. PATENT DOCUMENTS

| | | | |
|---|---|---|---|
| 4,073,439 | 2/1978 | Grataloup | 239/655 |
| 4,134,977 | 1/1979 | Greenberg | 424/78 |
| 4,150,109 | 4/1979 | Dick et al. | 424/28 |
| 4,158,051 | 6/1979 | Greenberg et al. | 424/28 |
| 4,189,467 | 2/1980 | von Bittera et al. | 424/14 |
| 4,195,075 | 3/1980 | Miller | 424/14 |
| 4,225,578 | 9/1980 | von Bittera et al. | 424/14 |
| 4,900,765 | 2/1990 | Murabayashi et al. | 523/122 |
| 4,992,275 | 2/1991 | Lush | 424/408 |

FOREIGN PATENT DOCUMENTS

| | | |
|---|---|---|
| 3730820 | 8/1988 | Fed. Rep. of Germany . |
| 1598644 | 8/1970 | France . |
| 2213014 | 8/1976 | France . |
| 2307456 | 11/1977 | France . |
| 2370572 | 6/1978 | France . |
| 2386254 | 11/1978 | France . |
| 2269859 | 3/1980 | France . |
| 2436563 | 7/1982 | France . |
| 2447679 | 10/1982 | France . |
| 2386253 | 12/1983 | France . |
| 2374853 | 1/1984 | France . |
| 2392606 | 9/1984 | France . |
| 2018593 | 10/1979 | United Kingdom ........ 424/408 |
| 1586258 | 3/1981 | United Kingdom . |

*Primary Examiner*—Thurman K. Page
*Assistant Examiner*—Neil Levy
*Attorney, Agent, or Firm*—Lowe, Price, LeBlanc & Becker

[57] ABSTRACT

A device enabling one or more active principles or substances to be released in a gradual and programmed manner, wherein the device can be obtained by:

a) preparing a powder comprising a resin or polymer matrix in which at least one suitable plasticizer is fully absorbed by heating the plasticizer and hot spraying it onto the matrix while it is being maintained in temperature, thereby saturating the resin with plasticizer;

b) cooling the powder obtained in a) to a temperature below 30° C;

c) cold mixing the powder obtained in b) with at least 5% of at least one carrier of active principle; then d) adding the active principle(s); and e) suitably forming the powder obtained in d) by any appropriate means, which device releases the active principle uniformly and completely.

The device further includes a covering made of a polymer which is impermeable to the active principle(s) and which covers a portion of the surface of the device.

A method of preparing the device and applications thereof to preparing medicines suitable for administration per os, to preparing medicines suitable for administration by skin contact, and to preparing antiparasite collars.

5 Claims, 1 Drawing Sheet

CONTROLLED RELEASE DEVICE, AND METHOD OF PREPARATION

This application is a continuation of application Ser. No. 07/634,848 filed Dec. 27, 1990, now abandoned.

The present invention relates to a device for enabling continuous and complete controlled release of chemical substances, including medicines, over a very long period of time, said release of active principals taking place at a determined rate, i.e. a more or less constant daily dose is released over the entire lifetime of the device, with release taking place from an insoluble polymer matrix to an appropriate zone of an animal or human body.

The present invention also relates to a method of preparing such a device.

BACKGROUND OF THE INVENTION

Numerous systems are known for controlled and programmed release of active principals.

They are all solid or semi-solid systems, e.g. of the tablet or suppository type having a composition which is defined so as to lead to the systems breaking up slowly, with breaking up itself being obtained either by a purely mechanical effect, or else by partial dissolution of one or more components forming the system in a liquid medium, e.g. constituted by body fluids.

It is also known to disperse the active principal throughout a solid substrate and to obtain programmed release thereof by diffusion through such a substrate.

In this case also, numerous systems are described:

there are "semipermeable" systems in which the active agent dissolved, suspended, or emulsified in an inert vehicle diffuses through a permeable membrane; and there are also compound systems in which the active agent diffuses from a more or less porous solid substrate constituted by a matrix based on polymers or copolymers.

Regardless of the system chosen, release speeds are maintained only for a very short length of time, and the system is therefore not suitable for prolonged use.

Solid systems are also known that are suitable for application by contact, in particular on the skin.

Particular mention may be made of devices suitable for gradually releasing a contact insecticide for protecting animals against parasites, and in particular against ectoparasites. Most of these devices are constituted by an insecticide included in a matrix of plastic material. The slow release of an ectoparasiticide substance (whether in vapor form or by deposition on the hairs of the animal) provides effective protection against parasites for several months.

Such anti-parasite devices constitute the subject matter of very many patents, and in particular the Applicants' French patents numbers FR 2 447 679, FR 2 269 859, and FR 2 307 456, and also the following patents: FR 2 436 563 in the name of Shell International Research; FR 2 370 572 and FR 2 392 606 in the name of A. H. Robins Company Inc.; FR 1 598 644 and FR 2 213 014 in the name of Robert Aries; and FR 2 374 853, FR 2 386 253, and FR 2 386 254, in the name of Bayer AG, and such devices are essentially constituted by three basic components:

an insecticide (or mixture of insecticides);

a matrix (generally based on a thermoplastic resin); and additives (such as plasticizers, pigments, stabilizing agents, or inert fills, etc. . . . . ).

Nevertheless, all prior art devices suffer from two major drawbacks:

they never release all of the active principal that they contain, and this may be important, or even essential, particularly with active principals that are expensive; and the active principal is never released at a constant rate, with a very large quantity of substance being released at the beginning of utilization, after which the release rate falls off very rapidly to become zero.

These drawbacks of the prior art are related, in particular, to the active principal being applied hot and then being absorbed or adsorbed by the resin, which means that a large amount of the active principal is retained by the resin (of the order of 30% to 70%, depending on circumstances). This major retention of the active principal in prior art devices is due, in particular, to the following facts:

when the active principal is a liquid, it behaves like a plasticizer for the resin (two-way interchange between the plasticizer and the active principal), and in this case the active substance is absorbed by the resin; and when the active principal is a solid, the plasticizer acts as a solvent therefor, such that the active principal is adsorbed by the plasticizer included in the resin.

Consequently, an object of the present invention is to provide a device which satisfies practical requirements better than previously known devices for the same purpose, and in particular to provide a device that releases all of the active principal contained in said device over varying, but predictable, durations, and above all making substantially constant daily release possible over the entire lifetime of the device.

SUMMARY OF THE INVENTION

The present invention provides a device enabling one or more active principals or substances to be released in a gradual and programmed manner, wherein the device can be obtained by:

a) preparing a powder comprising a resin or polymer matrix in which at least one suitable plasticizer is fully absorbed by heating said plasticizer and hot spraying it onto said matrix while it is being maintained in temperature, thereby saturating said resin with plasticizer;

b) cooling the powder obtained in a) to a temperature below 30° C.;

c) cold mixing the powder obtained in b) with at least 5% of at least one carrier of active principal; then d) adding the active principal(s); and e) suitably forming the powder obtained in d) by any appropriate means, which device releases the active principal uniformly and completely.

Unexpectedly, the device of the invention makes it possible to obtain total, uniform, and gradual release of the active principal since this substance is neither absorbed, nor adsorbed by the polymer matrix or resin; the method of preparation of the invention solves the problem of releasing all of the active principal from a polymer matrix:

by modifying the order and the conditions under which the various ingredients are combined; namely firstly resin and plasticizer, while hot, cooling down the resulting powder, and then adding the carrier of the active principal and the active principal(s), when cold; and by modifying the active principal by means of the active principal carrier in such a manner that a dry mixture is obtained which is suitable for the desired shaping.

Mixing the resin and the plasticizer while hot causes the pores of the resin to dilate, thereby making it possible to saturate the resin with plasticizer; thereafter, cooling the plasticized resin causes the pores of the resin to close and makes it inert relative to the active principal.

Adding a carrier of active principal and then the active principal, while cold, makes it possible to cause the active principal to be absorbed or adsorbed on said carrier and not in the resin.

In an advantageous embodiment of said device, the carrier of active principal is advantageously selected from the group comprising: sawdust, natural or synthetic fibers, and mineral fillers such as: barium sulfate, calcium carbonate, zeolites, diatomaceous earths, kaolin, talc, silica, hydrated calcium silicate, antimony trioxide, titanium oxide, and glass microbeads.

The Applicants have found that in order to enable the active principal to be released fully, the choice of carrier of active principal is very important and that it depends, in particular, on the nature of the active principal, on its chemical formula, and on its steric hindrance. It is also necessary to avoid any of the following compatibilities between the active principal and the carrier: chemical, since otherwise a portion or all of the active principal will be retained; physical, since if the carrier of active principal is too porous, it will trap the active principal and it will not be able to restore it; and mechanical, since the particle size of said carrier may interfere with the release of the active principal, particularly if the active principal is in solid form.

In another advantageous embodiment of said device, the plasticizer is selected from the group constituted, in particular, by: esters such as phthalates, adipates, sebacates, and phosphates.

In the context of the present invention, the term "plasticizer" is used to cover any compound (generally a liquid) that is compatible with the macromolecular matrix and that confers flexibility thereto.

The following may be mentioned in non-limiting manner as suitable plasticizers: isobutyl adipate, diethyl-2 hexyl adipate, diethyl-2 hexyl phthalate, and dibutyl phthalate.

In another advantageous embodiment of said device, it further includes at least one additive selected from the group constituted by: coloring, pigments, lubricants, antioxidizing agents, heat or ultraviolet stabilizers, pore-generating agents, deodorants, fragrances, other biocides, and attractors.

In another advantageous embodiment of said device, the matrix is made, in particular, from polymers or copolymers selected from the group constituted by: vinyl polymers, polyethylenes, polypropylenes, polyacetates, polyurethanes, and vinyl acetates.

The choice of said matrix depends on the active principal(s), on the other main components, and above all on the article and the use to which it is to be put.

In yet another advantageous embodiment of said device, it comprises, in terms of percentage of the weight of the total composition:
  between 10% and 60% resin or polymer matrix;
  between 5% and 40% plasticizer;
  between 3% and 80% active principal; and
  between 5% and 80% carrier of active principal(s).

In an advantageous disposition of this embodiment, said device comprises between 5% and 50% of carrier of active principal.

The respective quantities of the different components present in the device of the invention are a function of the quantity of active principal to be included.

The active principal may be in liquid form or in solid form. When in solid form, it may be converted to liquid form by adding an appropriate solvent, with the choice of solvent depending on the chemical nature of the active principal.

In a variant, the device of the invention further includes a polymer covering which is impervious to the active principal(s) and which partially covers the surface of the device as defined above.

Such a device, in which the covering is referred to as the "passive portion" and the device as defined above is referred to as the "active portion", has the advantage of directing the gradual, programmed, uniform, and complete relief of the active principal.

In this variant of the device, the covering is advantageously a polymer selected from the group constituted, in particular, by: vinyl polymers, polyethylenes, polypropylenes, polyacetates, polyurethanes, and vinyl acetates.

The present invention also provides a method of preparing said device, the method comprising the following steps:

a) preparing a powder containing the resin or polymer matrix in which the plasticizer is fully absorbed by heating the plasticizer and hot spraying it onto said matrix while it is being maintained in temperature, thereby saturating said resin with plasticizer;

b) cooling the powder obtained in a) to a temperature of less than 30° C.;

c) cold mixing the powder obtained in b) with at least one active principal carrier; then d) adding the active principal(s); and e) forming appropriately by any suitable means.

Such a method has the advantage of making it possible to obtain cold adsorption of the active principal(s) on the active principal carrier prior to being intimately mixed with the plasticized polymer matrix that has been cold stabilized and has thus become inert relative to the active principal.

The device may advantageously be presented in a form that can be taken by mouth, or else in the form of a collar, in particular an antiparasite collar.

The device may be formed in conventional manner for the person skilled in the art by casting, by injection molding, or by extrusion.

In an advantageous implementation of said method, the temperature suitable for hot spraying the plasticizer is about 70° C. to 80° C.

In another advantageous implementation of said method, the method further includes separate preparation of the covering (also known as the "passive portion") of the device using polymers selected from the group which comprises, in particular: vinyl polymers, polyethylenes, polypropylenes, polyacetates, polyurethanes, and vinyl acetates.

In this implementation, the "passive portion" or covering is made in conventional manner by casting, by injection molding, or by extrusion.

The "passive portion" and the "active portion" of said device may advantageously be made simultaneously with forming then preferably being obtained by co-extrusion.

Said device, constituting an active portion only, or an active portion in association with the passive portion, is particularly suitable for preparing medicines that are administrable per OS to preparing medicines that are administrable by cutaneous contact, and to preparing antiparasite collars.

BRIEF DESCRIPTION OF THE DRAWING

In addition to the above dispositions, the invention also includes other dispositions which appear from the following description relating to examples of implementations of the present invention, and the accompanying drawing in which.

Figure 1A:
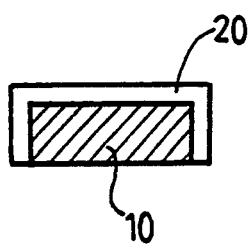
FIGS. 1a, 1b, and 1c are sections through various embodiments of the device of the invention including a covering.

It should nevertheless be understood that these examples are given purely to illustrate the invention, and that they do not constitute any kind of limitation.

DETAILED DESCRIPTION

The method of the invention may be implemented, in non-limiting manner, as follows: active portion: an intimate mixture is made of the resin with stabilizers and with lubricants, and the mixture is heated to about 70° C.-80° C. When the stabilized resin is at that temperature, plasticizer(s) previously heated to the same temperature as the resin is/are sprayed in the form of fine droplets, taking care to maintain the temperature of the resin. The plasticizer(s) is/are thus fully absorbed, and the plasticized product is in the form of a perfectly dry powder. The mixture is transferred mechanically into a cooling vessel which makes it possible to avoid having a hot mixture during the following operations, since a hot mixture could cause the resin to become desaturated, thereby running the risk of it jelling prematurely. When the mixture is thoroughly cooled, the carrier (s) of active principal is/are added and mixed in intimately. Active principals that are in liquid form are then sprayed as fine droplets into the mixture and are then adsorbed by the carrier, whereas active principals that are in solid form are intimately mixed with the remainder of the formulation. Other additives (coloring, pore-generating agents, fragrance, . . . ) are added to the mixture at the manufacturing stage which is most suitable for the nature of the additive.

Passive portion: the resin may be used unaltered or it may be mixed with other components such as stabilizers, plasticizers, or other substances improving its qualities, in particular its impermeability to the active-principal(s).

EXAMPLE 1

Same-sized collars for family pets are prepared by extrusion, the collars containing 15% by weight Diazinon (O,O-diethyl-O-(2-isopropyl-4-methyl-6-pyrimidinyl) phosphorothiorate), 3.5% stabilizers, lubricants, and coloring, isobutyl adipate, polyvinyl chloride (PVC), and a mixture of calcium carbonate and silica carriers of the active principal, in compliance with the manufacturing protocol specified above. Various quantities of carrier can be used, as can be seen from Table I below,

TABLE I

| TEST 1 | TEST 2 | TEST 3 | TEST 4 | TEST 5 | |
|---|---|---|---|---|---|
| 58% | 50% | 37% | 32% | 30.5% | PVC |
| 23.5% | 21.5% | 24.5% | 14.5% | 11% | DIBA |
| 0% | 10% | 20% | 35% | 38% | CaCO$_3$ |

TABLE I-continued

| TEST 1 | TEST 2 | TEST 3 | TEST 4 | TEST 5 | |
|---|---|---|---|---|---|
| 0% (*) | 0% (*) | 0% (*) | 0% | 2% | Silica |

PVC = polyvinyl chloride
DIBA = diisobutyl adipate
CaCO$_3$ = calcium carbonate
(*) heating was necessary to obtain a dry final mixture capable of being extruded.

The rate of Diazinon release was determined by causing six collars from each test to be worn by dogs of the beagle race, and a body weight lying in the range 9 kg to 11 kg. A 500 mg collar sample was taken from each animal at various different times and was analyzed by high performance liquid chromatography. Table II below shows the averages of the six values of Diazinon remaining per collar and per batch at various different times:

TABLE II

| TEST 1 | TEST 2 | TEST 3 | TEST 4 | TEST 5 | TIME (days) |
|---|---|---|---|---|---|
| 100% | 100% | 100% | 100% | 100% | 0 |
| 97% | 94.6% | 92.4% | 89.8% | 95.5% | 7 |
| 87.2% | 85.1% | 76.7% | 80.1% | 79.8% | 28 |
| 79.8% | 78% | 70.8% | 64.5% | 70.2% | 56 |
| 78.5% | 75.2% | 66.6% | 61.8% | 63.9% | 84 |
| 79.7% | 73.1% | 63.8% | 55% | 55% | 140 |
| stop | 74.7% | 61.9% | 51% | 42.3% | 196 |
| | stop | 60.2% | 47.2% | 31.3% | 252 |
| | | 60.5% | 42.1% | 17.0% | 308 |
| | | stop | 42.1% | 8.4% | 336 |
| | | | 41.9% | 0.3% | 364 |

The results show that the method of the invention facilitates the release of the insecticide. However, it was not possible to make collars without heating the mixture while inserting the insecticide for tests 1, 2, 3, and 4, and thus a portion of the insecticide is used as a plasticizer and as a result total elimination is not obtained, whereas in test 5 which includes an additional quantity of carrier it was possible to incorporate the insecticide cold and to obtain total release of the insecticide, the object of the invention.

EXAMPLE 2

In similar manner to Example 1, the following compositions defined in Table III below were made up in the form of collars and insecticide elimination was measured.

TABLE III

| | FORMULAS | | | | |
|---|---|---|---|---|---|
| | AMITRAZ | PVC | CaCO$_3$ | DOA | OTHER |
| TEST 1 | 9% | 56.4% | 0% | 31.1% | 3.5% |
| TEST 2 | 9% | 50% | 10% | 27.5% | 3.5% |

DOA = diethyl-2 hexyl adipate
*the mixture of Test No. 1 required heating to obtain a dry mixture.

The rate of Amitraz for which the chemical formula name is N'-(2,4-dimethylphenyl)-N-[[(2,4-dimethylphenyl)imino]methyl]-N -methylmethanimidamide, release was measured by causing six collars from each test to be carried by dogs of the beagle race, and of body weight lying in the range 9 kg to 11 kg. A 500 mg collar sample was taken from each animal at various times and analyzed by high performance liquid chromatography. The means of the six values for Amitraz remaining per collar at various given times are presented in Table IV below.

TABLE IV

| TIME (days) | ELIMINATION | | | | | |
|---|---|---|---|---|---|---|
| | 0 | 15 | 30 | 60 | 90 | 120 |
| TEST 1 | 100% | 79.9% | 69.9% | 60.2% | 59.7% | 59.4% |
| TEST 2 | 100% | 76.7% | 63.3% | 32.7% | 20.4% | 2% |

EXAMPLE 3

In similar manner to Example 1, the following compositions specified in Table V below were made up in the form of collars and insecticide elimination was measured as specified above in Example 2.

TABLE V

| | FORMULAS | | | | |
|---|---|---|---|---|---|
| | PROPOXUR | PVC | TALC | DOP/DBP | OTHER |
| TEST 1 | 9.5% | 57% | 0% | 30% | 3.5% |
| TEST 2 | 9.5% | 48% | 15% | 24% | 3.5% |

DOP/DBP = a mixture of diethyl-2 hexyl phthalate and dibutyl phthalate.
*the mixture of test no. 1 required heating to obtain a dry mixture.

The chemical formula name for Propoxur is 2-(1-Methylethoxy)phenol methylcarbamate.

TABLE VI

| TIME (days) | ELIMINATION | | | | | |
|---|---|---|---|---|---|---|
| | 0 | 15 | 30 | 60 | 90 | 120 |
| TEST 1 | 100% | 84.1% | 75.4% | 64.2% | 60.8% | 59.8% |
| TEST 2 | 100% | 72% | 56.9% | 34.3% | 18.9% | 2.8% |

EXAMPLE 4

A device was prepared including a covering, with the active portion being prepared as described in Example 1; the main compounds of the active portion have the following composition:

| | | |
|---|---|---|
| Diazinon | 15% | |
| DIBA | 11.5% | |
| CaCO₃ | 38% | |
| Silica | 2% | |
| PVC | 30.5% | | and the passive portion (covering) was made of unaltered polyurethane.

Figure 1B:
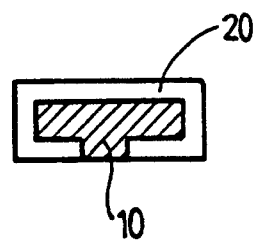
Figure 1C:
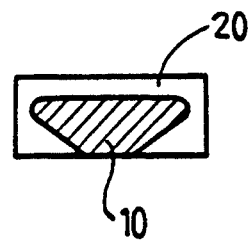

Such devices are shown in FIGS. 1a to 1c, where the respective passive portions 20 direct the release of the active principal contained in the active portions 10, in different manners.

The device was made up in the form of a collar by co-extrusion of the active and passive portions, and in this example, the section used was that shown in FIG. 1c. Elimination was measured as shown in Table VII below.

TABLE VIII

| | ELIMINATION | | | | |
|---|---|---|---|---|---|
| TIME (days) | 0 | 7 | 28 | 56 | 84 |
| % released | 0% | 4.5% | 9.9% | 15.7% | 22.2% |
| TIME (days) | 140 | 196 | 252 | 308 | 336 |
| % released | 35.2% | 48% | 61.1% | 73.6% | 80.5% |

As can be seen from the above, the invention is not limited in any way to the particular embodiments and applications that have been described in detail. On the contrary, the invention extends to any variant that may occur to the person skilled in the art without going beyond the context or the scope of the present invention.

I claim:

1. An antiparasite collar enabling one or more active agents to be released in a gradual and programmed manner, said device comprising a shaped body of: a powder comprising a resin, at least one plasticizer, at least one active agent carrier and at least one active agent;

wherein the improvement comprises preparing said device by:

a) preparing a powder comprising between 10 to 60 weight % of resin based on the total weight of resin, plasticizer, active agent carrier and active agent, said resin comprising polymers or copolymers selected from the group consisting of vinyl polymers, polyethylenes, polypropylenes, polyacetates, polyurethanes and vinyl acetates, heating said powder to a temperature between about 70° C. to 80° C.;

heating at least one plasticizer to about the same temperature as said powder and hot-spraying said plasticizer onto said powder, thereby saturating said resin with said at least one plasticizer to form a plasticized product in the form of a dry powder; wherein between 5 and 40 weight % of said at least one plasticizer based on the total weight of resin, plasticizer, active agent carrier and active agent is fully absorbed, wherein said plasticizer is an ester selected from the group consisting of phthalates, adipates, sebacates and phosphates;

b) cooling said plasticized product obtained in a) to a temperature below about 30° C. so that said plasticized product becomes inert relative to said at least one active agent;

c) cold mixing said plasticized product obtained in b) with between 5% and 80 weight % of at least one carrier of said at least one active agent based on the total weight of resin, plasticizer, active agent carrier and active agent, wherein said at least one carrier is selected from the group consisting of: sawdust, natural or synthetic textile fibers, and mineral fillers including barium sulfate, calcium carbonate, zeolites, diatomaceous earths, kaolin, talc, silica, hydrated calcium silicate, antimony trioxide, titanium oxide, and glass microbeads; said at least one carrier absorbing or adsorbing said at least one active agent in order to regulate the total release of said at least one active agent;

d) adding between 3 and 80 weight % of said at least one active agent based on the total weight of resin, plasticizer, active agent carrier and active agent, said at least one active agent being selected from the group consisting of o,o-diethyl-o-(2-isopropyl-4-methyl-6-pyrimidinyl) phosphoro-thiorate), N'-(2,4-Dimethylphenyl)-N-[[(2,4-dimethylphenyl-)imino]methyl]-N-(methylmethanimidamide and 2-(1-Methylethoxy)phenol methylcarbamate; and e) shape forming the powder obtained in d), which device releases said at least one active agent uniformly and completely.

2. The device according to claim 1, further including at least one additive selected from the group consisting of: pigments, lubricants, antioxidizing agents, heat stabilizers, ultraviolet stabilizers, pore-generating agents, deodorants, fragrances, biocides, and attractors.

3. The device according to claim 1, wherein said at least one active agent carrier is present in an amount between 5% and 50%.

4. The device according to claim 1, wherein said device further includes a polymer covering which is impervious to said at least one active agent selected from the group consisting of o,o-diethyl-o-(2-isopropyl-4-methyl-6-pyrimidinyl) phosphoro-thiorate), N'-(2,4-Dimethylphenyl)-N-[[(2,4-dimethylphenyl)imino)methyl]-N-methylmethanimidamide and 2-(1-Methylethoxy)phenol methylcarbamate, said polymer covering partially covering a surface of said device.

5. A device according to claim 4, wherein the covering is a polymer selected from the group consisting of: vinyl polymers, polyethylenes, polypropylenes, polyacetates, polyurethanes, and vinyl acetates.

* * * * *